(12) United States Patent
Cusimano-Reaston et al.

(10) Patent No.: US 8,117,047 B1
(45) Date of Patent: Feb. 14, 2012

(54) HEALTHCARE PROVIDER ORGANIZATION

(75) Inventors: Mary Rose Cusimano-Reaston, Las Vegas, NV (US); Phil Reaston, Las Vegas, NV (US)

(73) Assignee: Insight Diagnostics Inc., Las Vegas, NV (US)

( * ) Notice: Subject to any disclaimer, the term of this patent is extended or adjusted under 35 U.S.C. 154(b) by 832 days.

(21) Appl. No.: 11/787,249

(22) Filed: Apr. 16, 2007

(51) Int. Cl.
G06Q 50/00 (2006.01)
(52) U.S. Cl. .............................................. 705/3; 705/2
(58) Field of Classification Search .................. 709/217; 705/4, 2, 3; 382/118
See application file for complete search history.

(56) References Cited

U.S. PATENT DOCUMENTS

| | | | |
|---|---|---|---|
| 5,163,440 A | 11/1992 | DeLuca et al. | |
| 5,361,775 A | 11/1994 | Remes et al. | |
| 5,368,043 A | 11/1994 | Sunouchi et al. | |
| 5,462,065 A | 10/1995 | Cusimano | |
| 5,513,651 A | 5/1996 | Cusimano et al. | |
| 5,585,785 A * | 12/1996 | Gwin et al. | 340/575 |
| 5,662,118 A | 9/1997 | Skubick | |
| 5,722,420 A * | 3/1998 | Lee | 600/546 |
| 5,755,675 A | 5/1998 | Sihvonen | |
| 5,784,635 A * | 7/1998 | McCallum | 712/32 |
| 5,785,666 A | 7/1998 | Costello et al. | |
| 5,919,148 A | 7/1999 | Marko et al. | |
| 5,964,719 A | 10/1999 | Costello et al. | |
| 6,004,312 A | 12/1999 | Finneran et al. | |
| 6,159,147 A | 12/2000 | Lichter et al. | |
| 6,185,451 B1 * | 2/2001 | Richardson et al. | 600/546 |
| 6,265,978 B1 | 7/2001 | Atlas | |
| 6,280,395 B1 | 8/2001 | Appel et al. | |
| 6,322,502 B1 * | 11/2001 | Schoenberg et al. | 600/300 |
| 6,352,516 B1 | 3/2002 | Pozos et al. | |
| 6,440,067 B1 | 8/2002 | DeLuca et al. | |
| 6,441,747 B1 | 8/2002 | Khair et al. | |
| 6,493,578 B1 | 12/2002 | DeFeo | |
| 6,496,705 B1 | 12/2002 | Ng et al. | |
| 6,575,902 B1 | 6/2003 | Burton | |
| 6,597,944 B1 | 7/2003 | Hadas | |
| 6,631,297 B1 | 10/2003 | Mo | |
| 6,643,541 B2 | 11/2003 | Mok et al. | |
| 6,647,288 B2 | 11/2003 | Madill et al. | |
| 6,678,549 B2 * | 1/2004 | Cusimano et al. | 600/546 |
| 6,738,798 B1 * | 5/2004 | Ploetz et al. | 709/203 |
| 6,745,062 B1 | 6/2004 | Finneran et al. | |
| 6,816,603 B2 * | 11/2004 | David et al. | 382/107 |
| 6,856,833 B2 | 2/2005 | Finneran et al. | |
| 6,915,148 B2 | 7/2005 | Finneran et al. | |
| 6,917,825 B2 | 7/2005 | Finneran et al. | |

(Continued)

Primary Examiner — Gerald J. O'Connor
Assistant Examiner — Teresa Woods
(74) Attorney, Agent, or Firm — Sterne, Kessler, Goldstein & Fox, P.L.L.C.

(57) ABSTRACT

A business model for a healthcare provider organization (10) (HPO) which comprises a preferred provider network (PPO) or other membership agreement that allows individuals or groups to join via a membership contract. The contract allows the HPO (10) to provide a technical component of a medical evaluation or service (16). Additionally, the HPO (10) employs or retains the services of healthcare professionals (18) who participate in and monitor an evaluation of a patient (20) who can be at a remote location from the healthcare professional. The HPO (10) provides a medical diagnostic unit (24), which is known as an EFA-2, that allows the healthcare professional to receive data that pertains to the patient (20) via a real-time communication protocol (28), or the patient data is collected and stored on an electronic storage device (30). The healthcare professional then analyzes the patient data and issues recommended treatment.

1 Claim, 1 Drawing Sheet

U.S. PATENT DOCUMENTS

| | | | | |
|---|---|---|---|---|
| 6,917,829 | B2 * | 7/2005 | Kwong | 600/509 |
| 6,965,794 | B2 | 11/2005 | Brody | |
| 7,020,508 | B2 | 3/2006 | Stivoric et al. | |
| 7,027,621 | B1 * | 4/2006 | Prokoski | 382/118 |
| 7,058,438 | B2 | 6/2006 | Grace et al. | |
| 7,110,809 | B2 | 9/2006 | Nakada | |
| 7,127,279 | B2 | 10/2006 | Finneran et al. | |
| 7,130,673 | B2 | 10/2006 | Tolvanen-Laakso et al. | |
| 7,150,715 | B2 | 12/2006 | Collura et al. | |
| 7,160,253 | B2 | 1/2007 | Nissila | |
| 7,188,151 | B2 * | 3/2007 | Kumar et al. | 709/217 |
| 7,313,957 | B1 | 1/2008 | Kuramori et al. | |
| 7,363,069 | B2 | 4/2008 | Finneran et al. | |
| 7,381,185 | B2 | 6/2008 | Zhirnov et al. | |
| 7,409,242 | B2 | 8/2008 | Maekawa et al. | |
| 7,421,293 | B2 | 9/2008 | Kuramori et al. | |
| 7,433,733 | B2 | 10/2008 | Endo et al. | |
| 7,467,010 | B2 | 12/2008 | Kuramori et al. | |
| 7,486,987 | B2 | 2/2009 | Kuramori et al. | |
| 7,493,157 | B2 | 2/2009 | Gozani et al. | |
| 7,532,925 | B2 | 5/2009 | Kuramori et al. | |
| 7,574,369 | B1 * | 8/2009 | Borza | 705/2 |
| 7,602,301 | B1 | 10/2009 | Stirling et al. | |
| 7,627,358 | B2 | 12/2009 | Finneran et al. | |
| 7,628,761 | B2 | 12/2009 | Gozani et al. | |
| 7,634,315 | B2 | 12/2009 | Cholette | |
| 7,649,445 | B2 | 1/2010 | Kuramori et al. | |
| 7,693,572 | B2 | 4/2010 | Kuramori et al. | |
| 7,725,175 | B2 | 5/2010 | Koeneman et al. | |
| 7,764,990 | B2 | 7/2010 | Martikka et al. | |
| 7,767,149 | B2 * | 8/2010 | Maus et al. | 422/68.1 |
| 7,809,435 | B1 | 10/2010 | Ettare et al. | |
| 7,831,302 | B2 | 11/2010 | Thomas | |
| 7,860,562 | B2 | 12/2010 | Endo et al. | |
| 7,912,526 | B2 | 3/2011 | Finneran et al. | |
| 7,970,734 | B2 | 6/2011 | Townsend et al. | |
| 2005/0065819 | A1 * | 3/2005 | Schultz | 705/2 |
| 2005/0251421 | A1 * | 11/2005 | Chang et al. | 705/2 |
| 2006/0155173 | A1 | 7/2006 | Anttila et al. | |
| 2006/0190300 | A1 * | 8/2006 | Drucker | 705/2 |
| 2006/0265255 | A1 | 11/2006 | Williams | 705/4 |
| 2006/0271445 | A1 * | 11/2006 | Lee et al. | 705/26 |
| 2007/0016098 | A1 | 1/2007 | Kim et al. | |
| 2007/0027369 | A1 | 2/2007 | Pagnacco et al. | |
| 2007/0027388 | A1 | 2/2007 | Chou | |
| 2007/0033070 | A1 * | 2/2007 | Beck et al. | 705/2 |
| 2007/0130287 | A1 * | 6/2007 | Kumar et al. | 709/217 |
| 2007/0270665 | A1 | 11/2007 | Yang et al. | |
| 2008/0058668 | A1 | 3/2008 | Seyed Momen et al. | |
| 2009/0299210 | A1 | 12/2009 | Marcarian | |
| 2010/0106044 | A1 | 4/2010 | Linderman | |
| 2010/0137735 | A1 | 6/2010 | Hoppe | |

* cited by examiner

HEALTHCARE PROVIDER ORGANIZATION

TECHNICAL FIELD

The invention generally pertains to business models for healthcare organizations, and more particularly to a healthcare provider organization that provides medical services and a proprietary medical diagnostic unit which allows a healthcare professional to remotely analyze or examine a patient.

BACKGROUND ART

During the past decade, medicine and healthcare have experienced significant changes and improvements. With the advent of highly sophisticated medical devices, and the portability of such devices, healthcare delivery has become global. Global healthcare, aka global medicine, is primarily characterized by a doctor being at one location, and a patient being at another location. The distance between doctor and patient can be minimal, such as the doctor in one room and the patient in an adjoining room, or the distance can be significant, such as the doctor and patient each being on opposite sides of the earth.

The doctor is able to participate in a patient evaluation either in real-time via a video process, or the patient's data is acquired, stored and securely transported to the doctor or a medical facility for later review.

The benefits of a global healthcare provider are obvious. In the past, if a person in a remote location was injured or became ill, there could often be a delay of days or weeks before the person was brought to a doctor or medical facility. If the injury or illness was serious, the delay often resulted in the death of the person. Now it is possible to provide instant state-of-the-art medical care to the most remote location, thereby substantially increasing an injured or sick person's change of recovery or survival.

Additionally, many people have a personal doctor whom they trust and feel comfortable with a global healthcare provider will allow an individual to continue their relationship with a preferred doctor even if the individual or the doctor relocates.

DISCLOSURE OF THE INVENTION

A business model for a healthcare provider organization (hereinafter "HPO") that comprises a preferred provider network (PPO), or other membership agreement that allows individuals or groups to join via a membership contract. The contract allows the HPO to provide a technical component of a medical evaluation or service. Additionally, the HPO employs or retains the services of healthcare professionals who participate in and monitor an evaluation of a patient who can be at a remote location from the healthcare professional. The HPO provides a medical diagnostic unit, which is known as an Electro Functional Assessment (EFA) Unit, that allows the healthcare professional to receive data that pertains to the patient via a real-time communication protocol. The patient data is collected and stored on an electronic storage device. The healthcare professional then analyses the patient data and issues recommended treatment.

When the EFA diagnostic unit is located at a remote location from the healthcare professional, the HPO can train and provide medical assistants to perform the EFA diagnostic testing on a patient. The medical assistants can be registered nurses, licensed vocational nurses, medical assistant, exercise physiologists or other health or allied health providers.

In view of the above disclosure, the primary object of the invention is to provide a business model for a healthcare provider organization that utilizes a medical diagnostic unit to provide on-site or remote medical monitoring, testing and evaluation of a patient In addition to the primary object of the invention, it is also an object of the invention to provide a business model for a healthcare provider organization that:

does not violate franchise or healthcare laws and establishes only a member relationship to the healthcare provider organization, installs all necessary equipment, trains and supports the individuals or groups who join, and conducts evaluations on behalf of the healthcare professional, markets/advertises the healthcare provider organization's services to potential clients and patients, selects the tests/evaluations that are performed on each particular patient, chooses the most appropriate healthcare professional to test/evaluate a patient, allows the healthcare professional to participate in the technical component of the medical evaluation, and creates and issues a report, and bills for the service provided.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
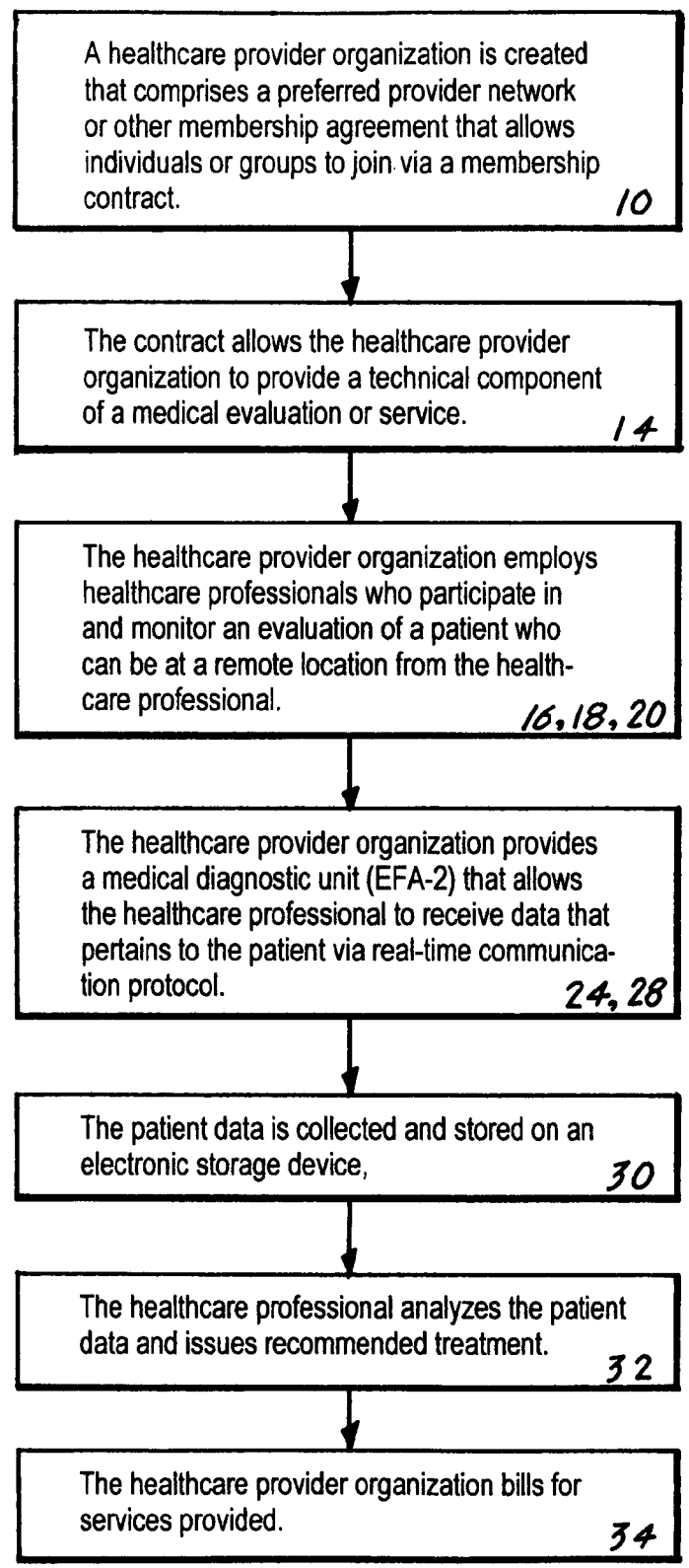
FIG. 1 is a block diagram of a business model for a healthcare provider organization.

The best mode for carrying out the invention is presented in terms of a preferred embodiment of a business model for a healthcare provider organization 10, (hereinafter "HPO 10"). As shown in FIG. 1, the HPO 10 is comprised of a preferred provider network (PPO) or other membership agreement that allows individuals or groups to join via a membership contract 14. The primary function of the contract 14 is to allow the HPO 10 to provide a technical component of a medical evaluation or service 16.

The HPO 10 employs or retains healthcare professionals 18 who participate in and monitor the evaluation 16 of a patient 20 who can be at a remote location from the healthcare professional 18. Typically, the healthcare professional 18 is a licensed doctor, although other medical professionals can also participate in the evaluation 16.

The HPO 10 provides a medical diagnostic unit 24 that allows the healthcare professional 18 to receive data that pertains to the patient 20 via a rear-time communication protocol 26. The medical diagnostic unit 24 is comprised of an Electro Diagnostic Functional Assessment (EFA) Unit or the later version EFA-2, which is disclosed in U.S. patent application Ser. No. 11/647,361.

The EFA-2 consists of a portable, integrated, self-contained, non-loading electronic unit that simultaneously monitors muscle activity with standard off-the-shelf silver-silver chloride electrodes. The muscle groups in a human or animal body, including cervical, cranial, thoracic, lumbosacral, as well as upper and lower extremities, are monitored. Specially designed electrodes are used to monitor cardiac function. The EFA-2 also combines a load cell and two strain gauges to determine a subject's lifting, pushing, pulling, gripping and pinching capabilities with range of motion ability. The EFA-2 functions in tandem with an integrated medical grade computer having a touch screen and/or attached keyboard and pointing device, and running a proprietary software program entitled EFA-2 Data Acquisition System, which correlates muscle activity with range of motion, cardiac activity, temperature, lifting, pushing, pulling, gripping and pinching. The design of the EFA-2 allows for electromyograph (EMG), range of motion (ROM), (spinal, upper and lower extremities, and hip and digits) grip assessment, pinch assessment, functional assessment, cardiac assessment, temperature assessment and nerve conduction studies to be conducted during a single testing session. The EFA-2 also allows for monitoring of cardiac, blood flow, heart rate, nerve conduction, EEG, as well as remote monitoring. In addition, the advantage of the EFA-2 is that it combines all physiological monitoring for diagnostic purposes with site specific treatment modalities. This is accomplished by integrating the electrical stimulation, ultrasound capabilities and/or massage of the EFA-2.

As disclosed above, the EFA is utilized to perform the medical evaluation or service 16. Depending on the relationship between the HPO 10 and the healthcare professional 18, (i.e., if the healthcare professional 18 in a member of the HPO 10), the EFA unit is either purchased by the healthcare professional 18, rented or leased by the healthcare professional, or given to the healthcare professional 18. If the healthcare professional 18 becomes a member of the HPO 10 (or the PPO), the EFA unit is a supplied element of the membership contract 14. The most significant benefit of utilizing the EFA is that it can be at a remote location from the healthcare professional 18. The actual distance that the EFA, and therefore the patient, can be located away are vary from minimal, such as the patient and healthcare professional in adjoining rooms, or substantial, such as the patient located on a different continent. This provides tremendous benefits, such as allowing people who live in under-developed or remote areas of the world to quickly and easily receive state-of-the-art medical attention. Some additional benefits are:

1) a person can consult and be treated by their personal physician regardless of where they are. This is important for people who travel or people who have moved to a new location but have an established relationship with a particular physician.

2) an EFA unit can be placed at a location that facilitates its use for specialized injuries, such as sports injuries and medicine, and 3) an EFA unit can be placed in a mobile environment, such as an airplane, train, subway, city bus, etc. In some respects, this would be the equivalent of having a physician present in any mobile environment, thereby providing immediate emergency medical attention to travelers. An EFA unit could even be placed in ambulances as an addition to the current medical communication systems that are in use. The location when the EFA is placed is usually selected by the HPO 10, especially when the healthcare professional 18 who is using the EFA is a member of the HPO 10.

Typically, when the EFA unit is located in a remote location, a medical assistant 26 will be present to assist in preparing a patient for evaluation and to operate the EFA. Preferably, the medical assistance 26 will be a registered nurse, but additionally, other medical assistants such as a licensed vocational nurse, general medical assistant, exercise physiologist, or other health or allied health professionals can be employed.

Once a patient 20 has been evaluated by the EFA-2's testing protocols, the patient's data is sent to the healthcare professional 18 via a rear-time communication protocol 28.

The communication protocol 28 is preferably comprised of a secure, encrypted Internet connection. Additionally, a secure dedicated phone line, such as an ISDN line, can also be utilized. Since the communication protocol 28 is real-time, the healthcare professional 18 can view the evaluation and determine the best treatment immediately.

If for some reason the healthcare professional 18 is unable to view the evaluation in real-time, the patient data is collected and stored on an electronic storage device 50.

It should be noted, that the patient data is also typically collected and stored when a real-time evaluation occurs. As with the majority of medical procedures, a patient's data must be collected and stored to provide a record of injury and illness, and to provide accurate patient billing for the services provided.

A common scenario will be that if a patient's injury or illness is not traumatic and/or immediately life-threatening, it will be easier and more economical for the healthcare professional to evaluate the patient's EFA-2 data at the healthcare professional's convenience.

The electronic storage device 30 for collecting and storing the patient data is selected from the group consisting of a computer, an external/stand-alone hard drive, a compact disc (CD) recorder, a digital video disc (DVD) recorder, an optical media recorder, or a hard disc recorder.

Regardless of whether the healthcare professional 18 analyzes the patient data in real-time or at a convenient later time, the healthcare professional 18 will determine the appropriate treatment 32 and convey this information to the patient 20 himself or to the medical assistant 26 who is operating the EFA-2 at the remote location with the patient. Obviously, if the patient is in need of immediate, emergency medical treatment, the appropriate steps will be taken by the healthcare professional 18 and/or the medical assistant 26.

Once the medical evaluation is complete, if the healthcare professional 18 is a member of the HPO 10, the HPO 10 will provide a bill for services provided to the patient or the patient's insurance company. The bill for services 34 comprises: analyzing the patient data, issuing a report for medical services or treatments that are recommended, patient data management (including collection and storage of the data), and medical supplies utilized during the patient evaluation.

When the healthcare professional 18 is a member of the HPO 10, the membership contract 14 is designed to incorporate the following four principles:

Principle #1 The healthcare professional 18 has a unique specialty, expertise and/or equipment, and desires to promote those services worldwide.

Principle #2 The HPO 10 agrees to provide the healthcare professional member with all the necessary equipment, training, support and expertise necessary to carry out the evaluation of patients.

Principle #3 The healthcare professional member agrees to abide by the membership contract, and to maintain all the necessary expertise to perform the evaluations, and Principle #4 The membership contract does not violate franchise or healthcare laws and establishes only a member relationship with the healthcare professional via the HPO 10.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

The invention claimed is:

1. The method for the HPO comprises:

Accessing wherein said HPO employs or contracts with the healthcare professionals who are selected from the group consisting of a licensed doctor, or a medical assistant or other medical professional further selected from the group consisting of registered nurses, licensed vocational nurses, medical assistants, exercise physiologists and other health or allied health professionals that participate the diagnostic unit, monitoring an evaluating of a patient who is trained to operate the medical diagnostic unit, operating wherein the medical diagnostic unit comprises a device to include EMG, ROM, FA, grip and pinch, operating wherein the medical diagnostic unit that comprises a device to include EMG, ROM, FA, grip and pinch can be located at a remote location from said HPO, providing for use wherein said HPO the medical diagnostic unit that comprises EMG, ROM, FA, grip and pinch that allows said HPO to receive patient data via a real-time communication protocol or upload of data for analysis via the internet, dedicated telephone line, or stored on an electronic storage device that is transmitted to HPO, collecting for use wherein the collected data is on an electronic storage device or transmitted and the HPO professional at a remote location from said HPO, analyzing the patient data and issues a recommended treatment or analysis, billing wherein said HPO for services for the device that consists of EMG, ROM, FA, grip and pinch, analyzing the patient data and issuing data is from the device for EMG, ROM, FA, pinch and grip, reporting wherein the HPO issues for medical services provided or treatments recommended, managing patient data from device for EMG, ROM FA grip and pinch.

* * * * *